(12) United States Patent
Curtis

(10) Patent No.: US 7,090,700 B2
(45) Date of Patent: Aug. 15, 2006

(54) DEVICE FOR OFFSETTING PROSTHETIC COMPONENTS

(75) Inventor: Michael J. Curtis, Green Bay, WI (US)

(73) Assignee: American Prosthetic Components, Inc., Green Bay, WI (US)

( * ) Notice: Subject to any disclaimer, the term of this patent is extended or adjusted under 35 U.S.C. 154(b) by 79 days.

(21) Appl. No.: 10/691,925

(22) Filed: Oct. 24, 2003

(65) Prior Publication Data

US 2005/0089363 A1    Apr. 28, 2005

(51) Int. Cl.
*A61F 2/62* (2006.01)
(52) U.S. Cl. .................. 623/38; 403/118; 403/381
(58) Field of Classification Search ............. 623/38; 403/118, 381
See application file for complete search history.

(56) References Cited

U.S. PATENT DOCUMENTS

| 1,302,336 | A | * | 4/1919 | Erickson ................. 623/38 |
| 5,405,347 | A | * | 4/1995 | Lee et al. ................ 606/54 |
| 5,800,565 | A | * | 9/1998 | Biedermann ............. 623/38 |
| RE36,521  | E |   | 1/2000 | Hiemisch |
| 6,033,440 | A | * | 3/2000 | Schall et al. ............. 623/38 |

FOREIGN PATENT DOCUMENTS

| CH | 638 095 A5 | * | 9/1983 | ......... 623/38 |
| DE | 39 37 379 A1 | * | 5/1991 | |
| GB | 167465 | * | 10/1922 | ......... 403/381 |

OTHER PUBLICATIONS

English translation of CH 638 095 A5.*
Hosmer Dorrance Corporation, product brochure, pp. H127-H132, publication date unknown.
Otto Bock, product description of lower limb prothetics adapters, viewed at www.ottobockus.com/products/op_adapters.asp on Oct. 22, 2003 (Three pages).

* cited by examiner

*Primary Examiner*—David H. Willse
(74) *Attorney, Agent, or Firm*—Brannen Law Office, LLC

(57) ABSTRACT

An offset alignment device with a longitudinal axis is provided that can offset two prosthetic components a selected distance along an alignment axis that is selectably oriented in a plane that is generally perpendicular to the longitudinal axis, and can also adjust the distance between the two prosthetic components in a direction generally parallel to the longitudinal axis. The present invention comprises first and second members. The first member has a channel and the second member has a bar for being adjustably connected to the channel along the alignment axis. A set screw can be through a hole in the wall of the channel in a direction generally perpendicular to the alignment axis to contact the bar and hold it stationary within the channel. One or both of the first and second members can be rotatably connected to one or both of the first and second prosthetic components, respectively.

7 Claims, 11 Drawing Sheets

BACKGROUND MATERIAL

BACKGROUND MATERIAL

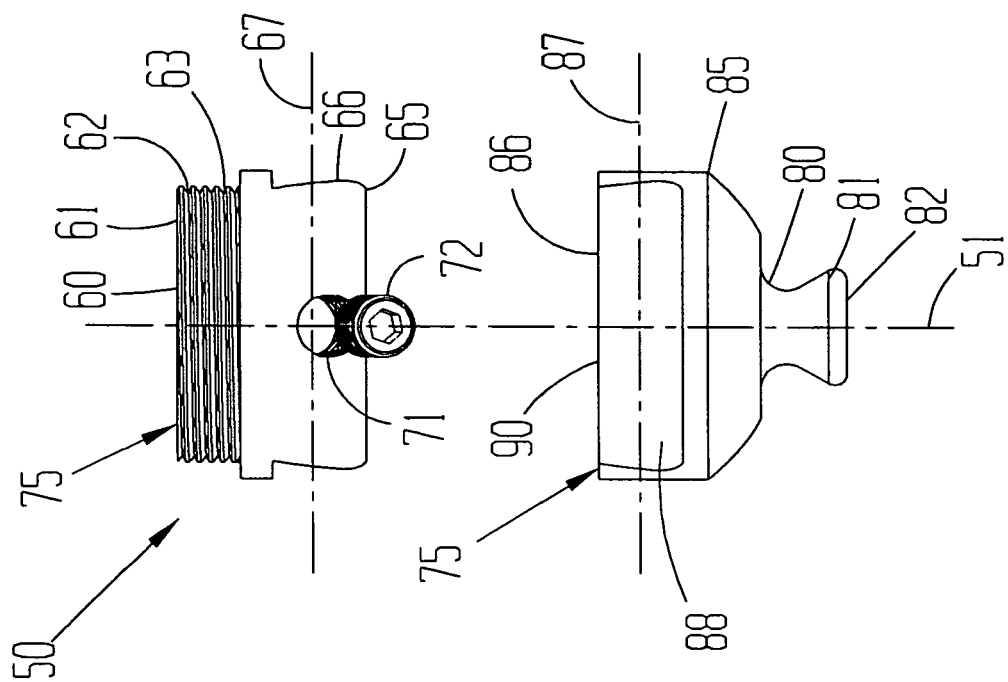
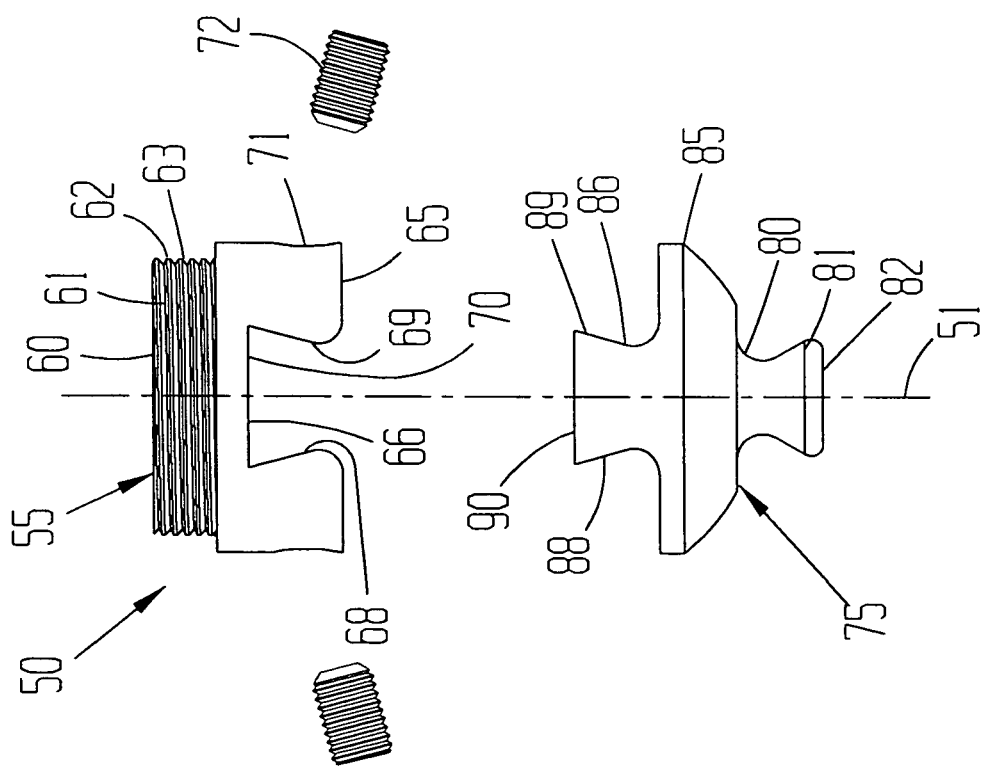

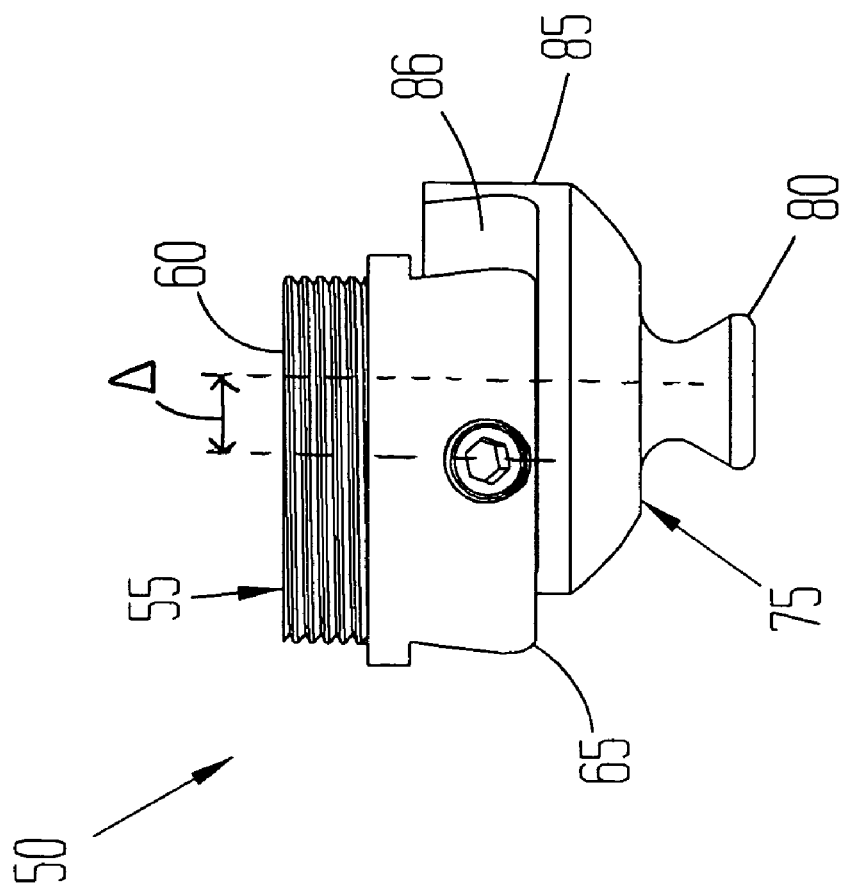
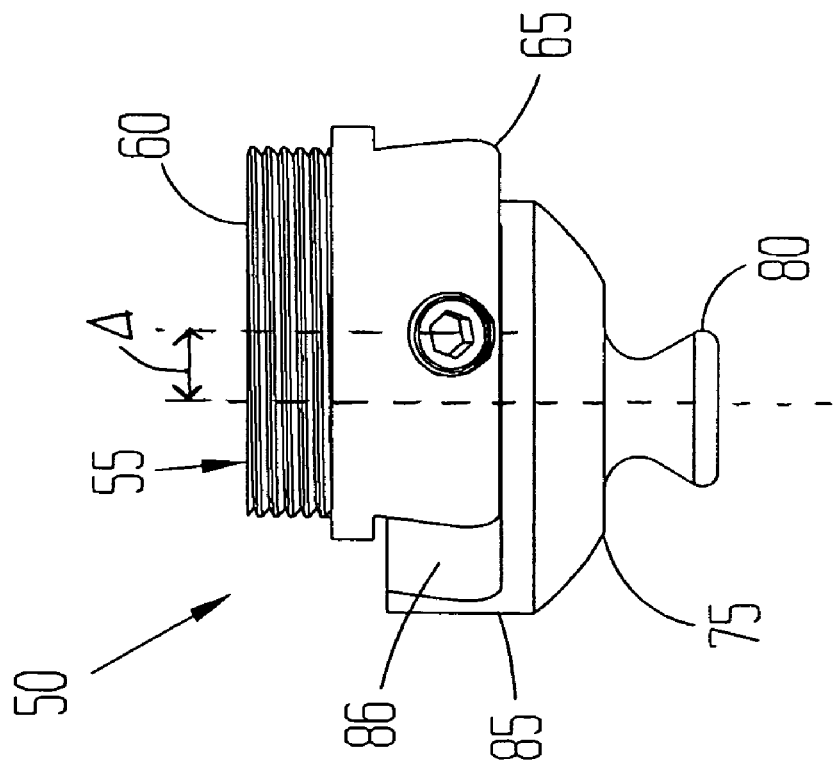

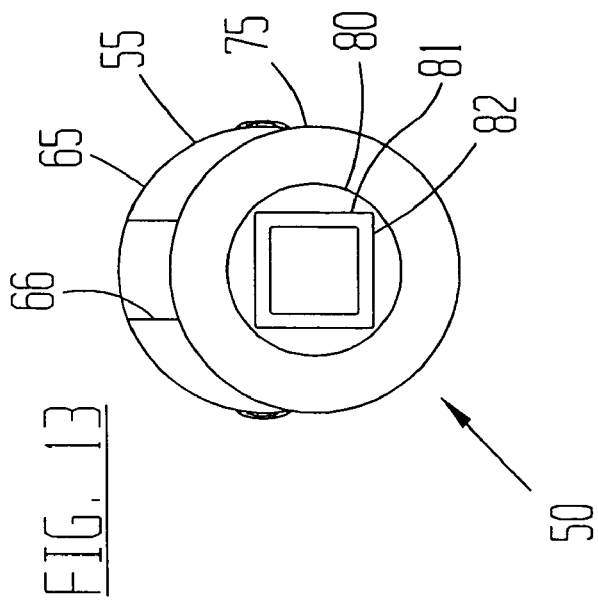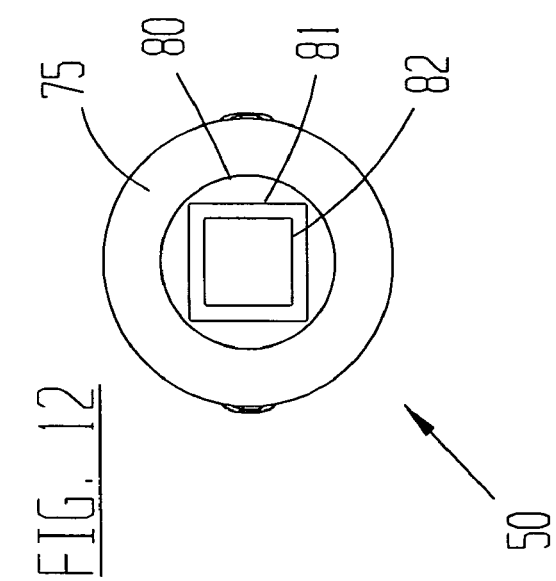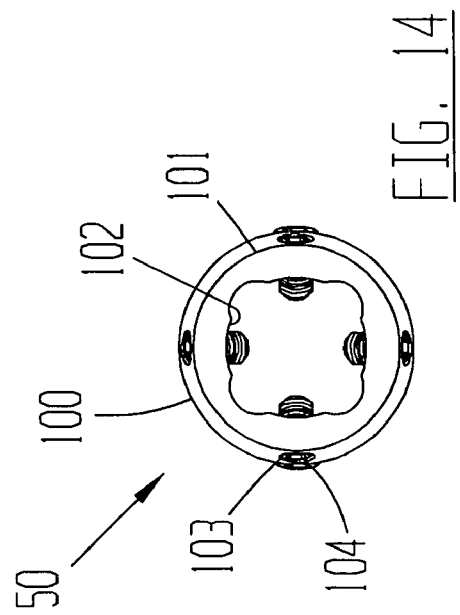

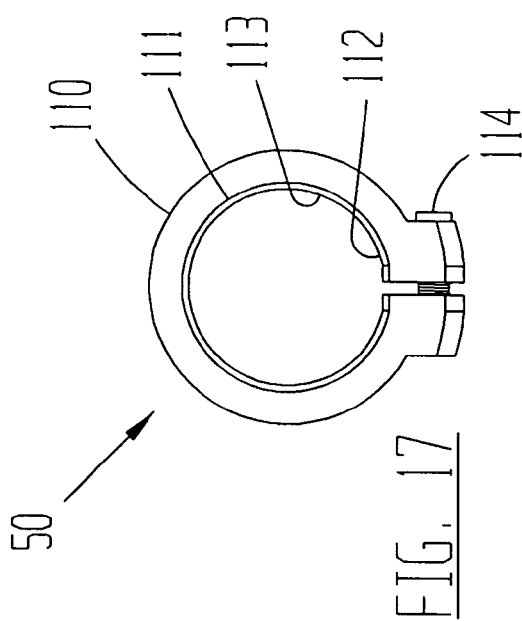
FIG. 16
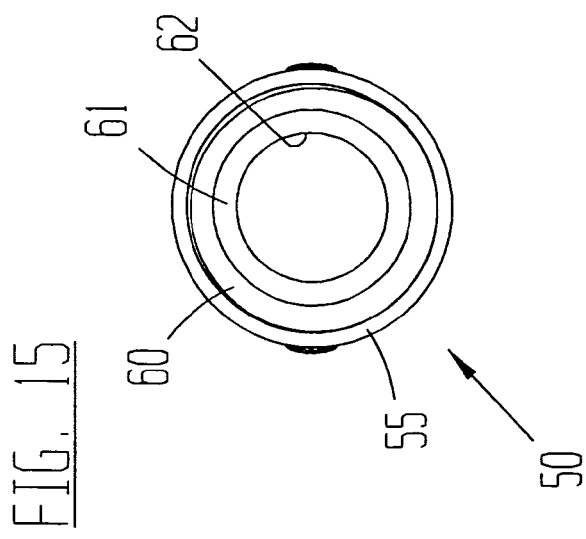
FIG. 17
FIG. 15

DEVICE FOR OFFSETTING PROSTHETIC COMPONENTS

BACKGROUND OF THE INVENTION

1. Field of the Invention

The present invention relates to a device for offsetting two prosthetic components that are connected to opposite ends of the present invention wherein the first prosthetic component is offsetable in both the anterior-posterior and the lateral-medial directions from the second prosthetic component a selected distance along a single offsetting axis.

2. Description of the Related Art

Sometimes, due to accidents, health problems, birth defects, etc., people 5 need to have a limb 6 amputated. The amputated limb 6 terminates in a stump 7. In general, a socket 10 can be formed for any particular stump 7. Those sockets 10 are well known in the art, and each socket 10 has a central axis 11.

Fortunately for people requiring a prosthetic limb, much advancement has been made in the field of prosthetic limbs. Patients now have many choices, including endoskeletal and exoskeletal prosthetic limbs. The present invention relates generally to endoskeletal prosthetic limbs. That is, limbs comprised of structural components and that may have an optional aesthetic outer shell.

In the case of a prosthetic leg and foot combination, it is desirable that the prosthetic components of the leg be in predetermined angular alignment with respect to the prosthetic components of the foot. This can be accomplished by using angular alignment devices. One device of this type is a pyramidal adapter for use with a fixed angle connector, and is manufactured by Otto Bock having part number 4R56. This device, as well as other alignment devices, may work well for their intended purpose, but their use carries with them some undesirable consequences. Notably, even if proper angular alignment of the lower components is achieved with these types of devices, the lower components may be offset from the upper components and from the person's residual limb in the lateral direction 15, the medial direction 16, the anterior direction 17 and/or the posterior direction 18.

The lower components can be out of alignment with the upper prosthetic components or the residual limb for other reasons as well. For example, the particular geometry of a person's limb 6 and stump 7 may cause the prosthetic components to be in an improper offset alignment, even if the prosthetics are connectable to the stump in a proper angular alignment.

The person's ability to comfortably walk can be compromised when the prosthetic components are in an offset alignment. One problem that occurs when the prosthetic components are offset is that the person's gait is affected. This is most prevalent when the prosthetic components are offset in either of the anterior or posterior direction.

Another problem associated with offset prosthetic components is that the person's weight may not be centered over the lowermost prosthetic components. This can affect not only the person's comfort, but also can cause unintended stress concentrations to develop within the prosthetic limb. This may lead to damage to or failure of the prosthetic limb.

Some advances have been made in attempting to overcome the drawbacks. For example, U.S. Pat. No. RE 36,521 to Hiemisch discloses a connecting part between leg prosthesis components. The connecting part has an adjusting element eccentrically positioned upon a rectangular flange. A user can select how to orient the flange with respect to the prosthesis components. However, there are only four possibilities that the flange can be oriented to with respect to a component connected to the flange. Hence, the connecting part provides for only limited adjustability, and provides for no adjustability other than due to the interfaces between the connecting part and the other prosthetic components.

A pair of components having dovetail connections is made by Hosmer Dorrance Corporation under the name Spectrum Alignment System. Examples of these components include a pyramid receiver with female dovetail for connecting to a pyramid receiver with male dovetail. A side shift screw is provided. The side shift screw has a head with a rib that rests in a groove in the female dovetail section. The threaded end of the screw is received within a hole in the male dovetail section. The screw head remains laterally stationary relative to the female dovetail section as the screw is twisted. However, the male dovetail section translates towards or away from the screw head as the screw is twisted, depending on which way the screw is twisted. Three screws and ball bearings are shown to guide the male end within the female end. The ball bearings are anti-friction devices that reduce friction between the female and male dovetail sections, which encourage movement of the male end within the female end when the side shift screw is twisted. The structural integrity of the dovetail connection is determined solely by the strength of the ribs on the screw head. If the screw head fails, the entire component could fail.

A further undesirable aspect of the Hossmer Dorrance Corporation components is that an adapter is needed to allow for adjustments to be made in both the lateral-medial directions and the anterior-posterior directions. In this regard, one pair of male and female dovetail components are needed for adjustment in each of the lateral-medial and anterior-posterior directions. These components are not shown to be capable of adjustment in the both the lateral-medial directions and the anterior-posterior directions by making an adjustment along a single axis.

A still further undesirable aspect of the Hossmer Dorrance Corporation components is that those components are not shown to be extendable or adjustable in a direction generally parallel to the longitudinal axis of the prosthetic components that they connect to. Due to this lack of adjustability, the Hossmer Dorrance Corporation components are incapable of being used to selectably adjust the length of a prosthetic limb. This may lead to unsatisfactory results unless the other components used in combination with the Hossmer Dorrance Corporation components are capable of making longitudinal adjustments, or unless the other components are exactly properly sized, so that the prosthetic limb will have a correct length.

Thus, there exists a need for an offset alignment device that solves these and other problems.

SUMMARY OF THE INVENTION

The present invention relates to an offset alignment device with a longitudinal axis that is capable of singularly offsetting two prosthetic components a selected distance along an alignment axis that is selectably oriented in a plane that is generally perpendicular to the longitudinal axis, and is also capable of adjusting the distance between the two prosthetic components that are connected to the present invention in a direction generally parallel to the longitudinal axis of the offset alignment device.

This is accomplished by providing a first member that is connectable to a first prosthetic component. The first member has an end comprising a channel. A second member is also provided, and is connectable to a second prosthetic component. The second member has a bar for being adjustably connected to the first member along an alignment axis. At least one set screw can be through a hole in the wall of the channel in a direction generally perpendicular to the alignment axis to contact the bar and hold it stationary within the channel.

One or both of the first and second members can be rotatably connected to one or both of the first and second prosthetic components, respectively. In this regard, the alignment axis can be adjusted to any desired orientation lying within a plane generally perpendicular to the longitudinal axis of the offset alignment device. Therefore, adjustments can be made in both the lateral-medial and the anterior-posterior directions by adjusting the present invention along a single axis.

A further advantage of the present invention is that it can be used to adjustably displace the first prosthetic component relative to the second prosthetic component. The alignment axis will be in its desired alignment in the plane generally perpendicular to the longitudinal axis each ½ turn of the present invention on the threaded end of first or second prosthetic component. This adjustability allows the present invention to correct for imperfect length determinations of the other prosthetic components, such as a pylon.

Other advantages, benefits, and features of the present invention will become apparent to those skilled in the art upon reading the detailed description of the preferred embodiments of the present invention and studying the drawings.

BRIEF DESCRIPTION OF THE DRAWINGS

FIG. 5 is an exploded end view of the present invention shown in FIG. 4.

FIG. 6 is an exploded side view of the present invention shown in FIG. 4.

FIG. 10 is similar to FIG. 9, but shows the present invention in a first offset alignment.

FIG. 11 is similar to FIGS. 9 and 10, but shows the present invention in a second offset alignment.

FIG. 12 is a bottom view of the present invention shown in FIG. 9.

FIG. 13 is a bottom view of the present invention shown in FIG. 11.

FIG. 14 is a bottom view of an alternative embodiment of the present invention showing a pyramidal receiver.

FIG. 15 is a top view of the present invention shown in FIG. 9.

FIG. 16 is a top view of the present invention shown in FIG. 11.

FIG. 17 is a top view of an alternative embodiment of the present invention showing an internally threaded clamp.

DETAILED DESCRIPTION OF THE PREFERRED EMBODIMENTS

While the invention will be described in connection with a preferred embodiment, it will be understood that it is not intended to limit the invention to that embodiment. On the contrary, it is intended to cover all alternatives, modifications and equivalents as may be included within the spirit and scope of the invention as defined by the appended claims.

Figure 1:
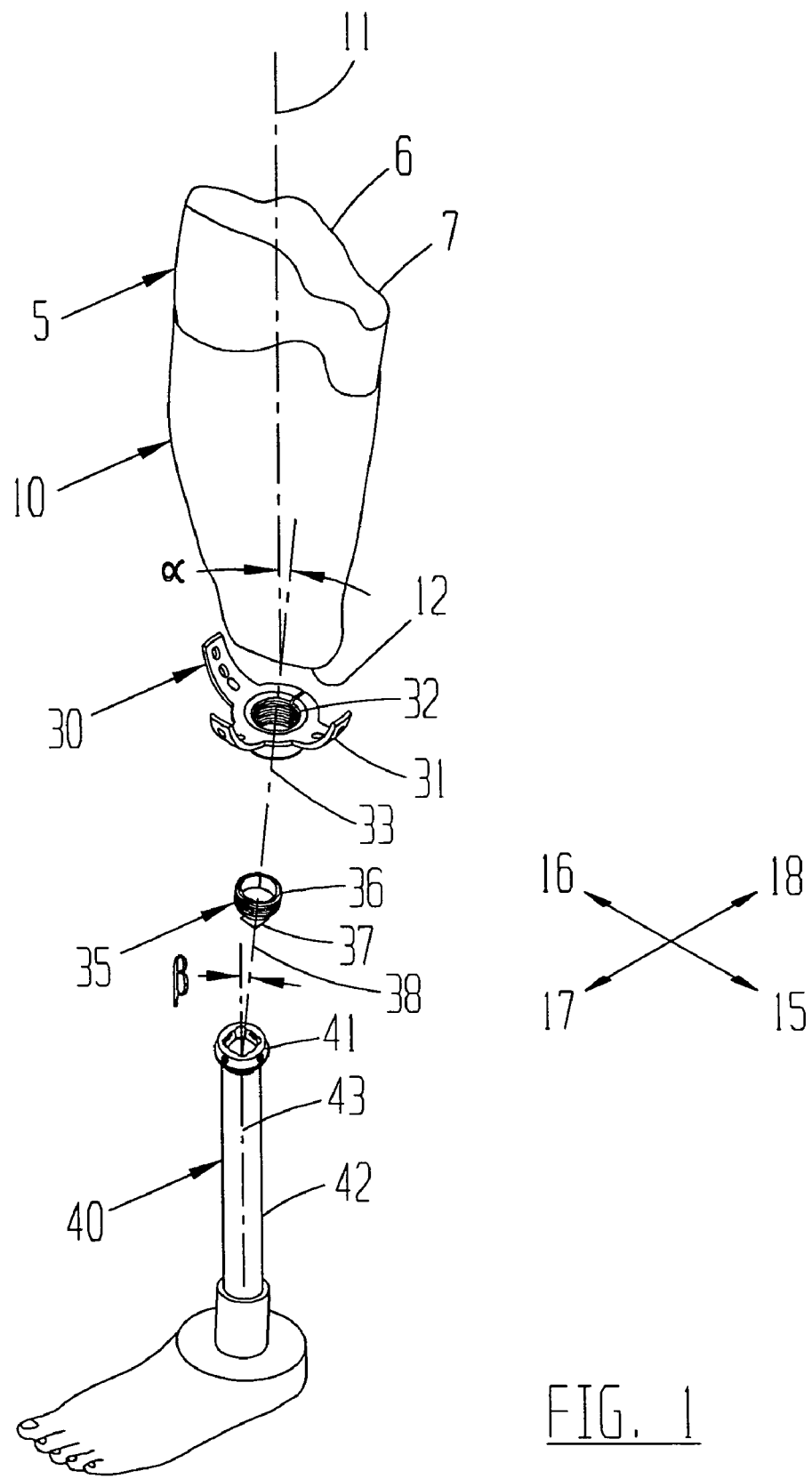
FIG. 1 is an exploded perspective view showing a configuration of existing prosthetic components.
Figure 2:
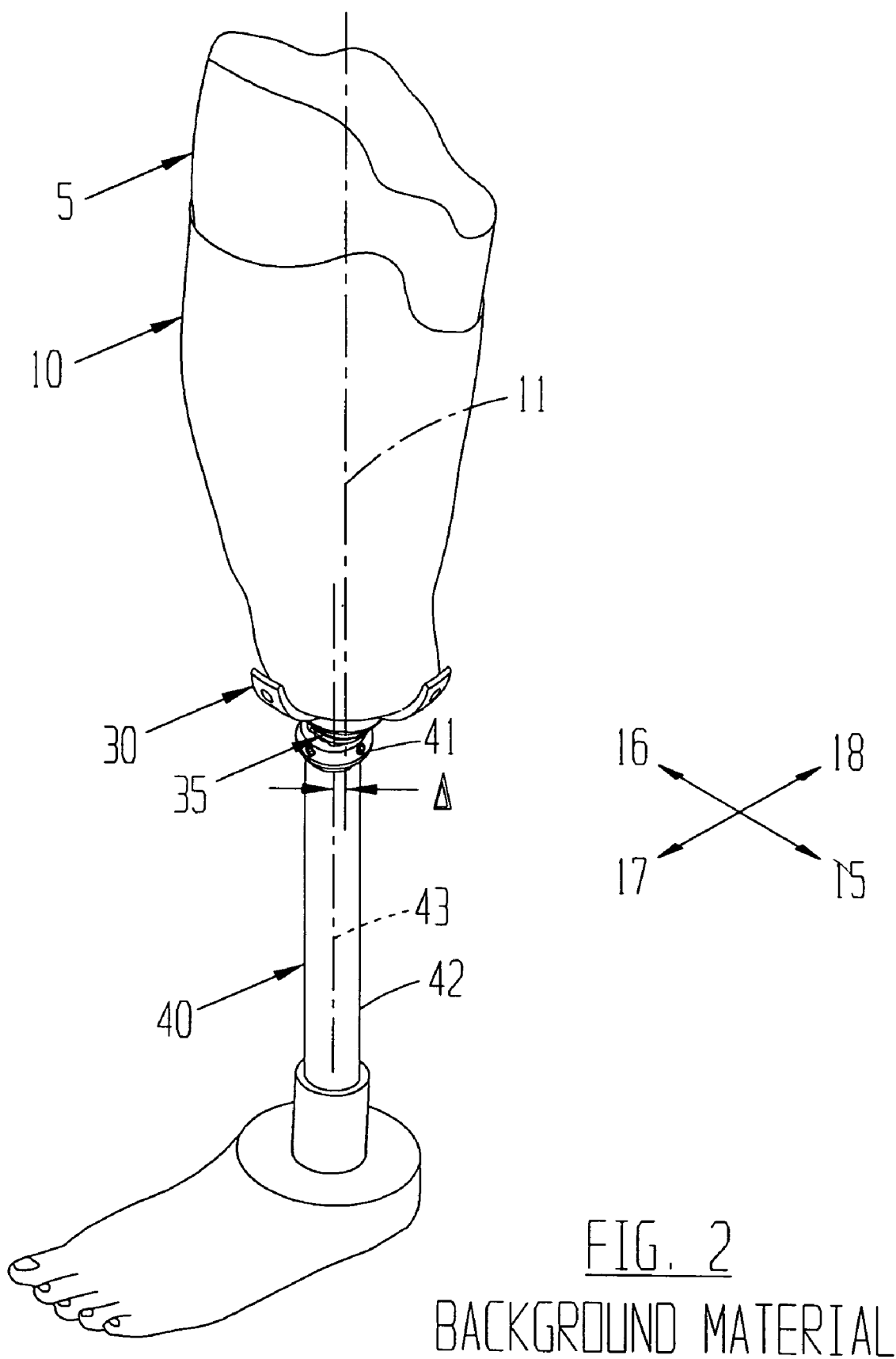
FIG. 2 is a perspective view of the existing components shown in FIG. 1 showing an offset of the components when assembled.

The present invention is intended for use with a prosthetic limb. A person 5 having a limb 6 terminating in a stump 7 may have prosthetic limb. A conventional set up is shown in FIGS. 1 and 2, where the prosthetic limb has a socket 10 with a socket central axis 11 and an end 12. The socket 10 can be angularly offset from the remainder of the prosthetic component by angle alpha. A three prong adapter 30 having prongs 31, an internally threaded end 32 and a central axis 33 can be connected to the socket 10.

Another component, such as a pyramidal adapter 35 can be connected to the three prong adapter 30. The pyramidal adapter 35 has an externally threaded end 36, a pyramidal end 37 and a central axis 38. The externally threaded end 36 is connected to the internally threaded end 32 of the three prong adapter 30. When the pyramidal adapter 35 and the three prong adapter 30 are connected, their respective central axis 33 and 38 are generally parallel.

A pylon with a fixed receiver 40 can be further connected to the pyramidal adapter 35 in a conventional manner. The pylon with a fixed receiver 40 has a fixed receiver 41 for connected to the pyramidal end 37 of the pyramidal adapter 35. The pylon with a fixed receiver 40 further comprises a pylon 42 having a central axis 43. The central axis 43 can be angularly offset from the central axis 38 of the pyramidal adapter 35 by angle beta. A person can adjustably select angle beta such that it is equal and opposite of angle alpha. In this regard, central axis 43 of the pylon with a fixed receiver 40 can be made parallel to, albeit offset from, the central axis 11 of the socket. As best shown in FIG. 2, this offset amount delta, can be in the lateral direction 15, the medial direction 16, the anterior direction 17 and the posterior direction 18.

Figure 4:
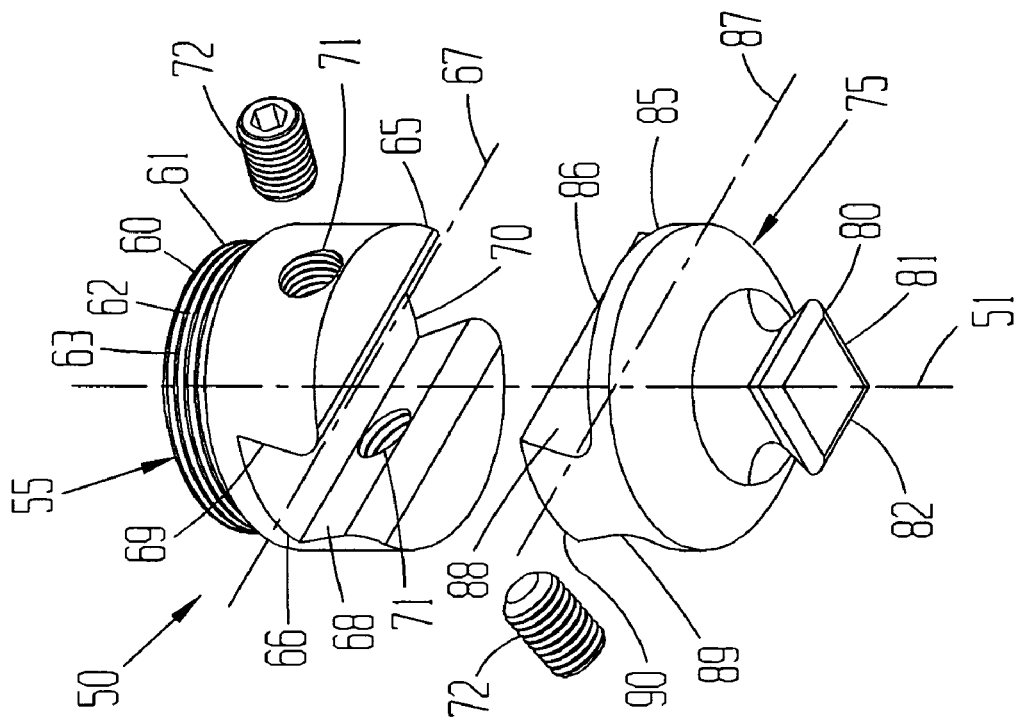
FIG. 4 is an exploded perspective view of the present invention.
Figure 3:
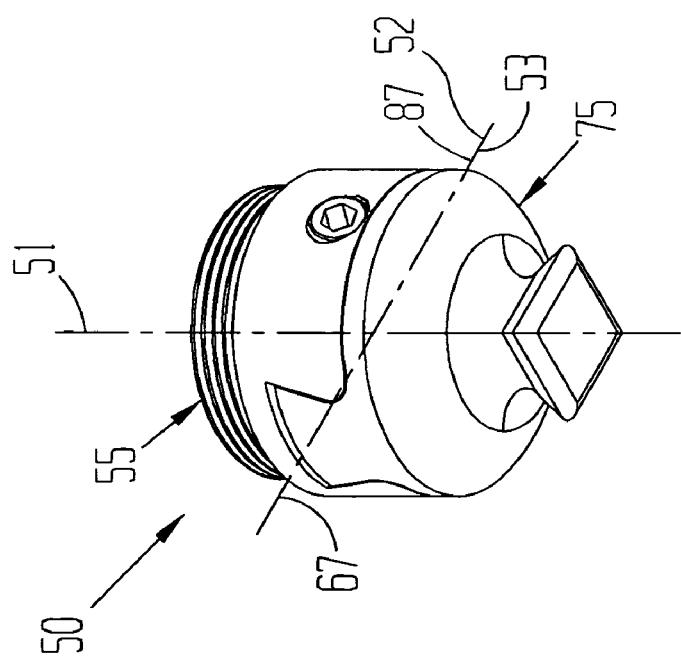
FIG. 3 is a perspective view of the present invention.
Figure 9:
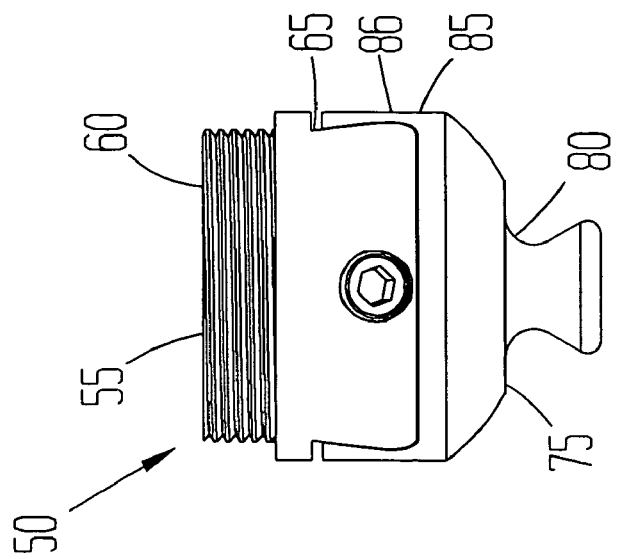
FIG. 9 is a side view of the present invention shown in FIG. 3 and in an aligned position.
Figure 8:
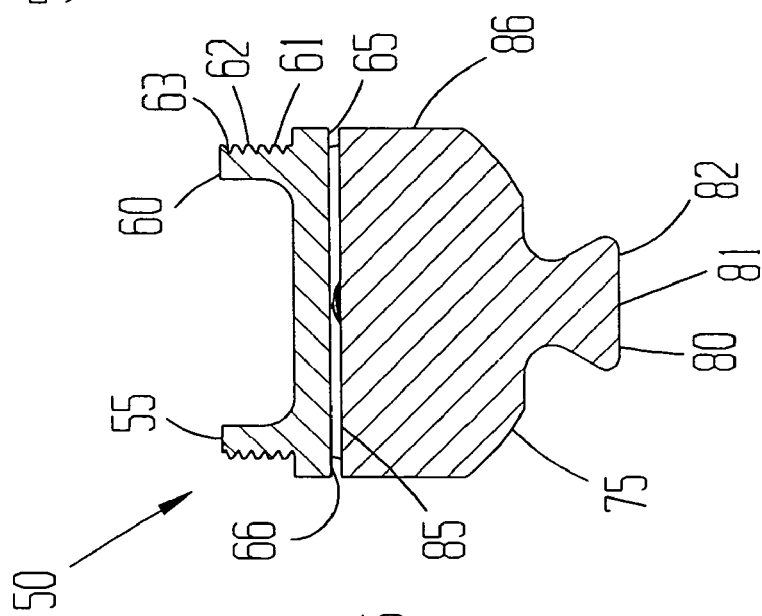
FIG. 8 is a cross-sectional view of the present invention taken along line 8—8 in FIG. 7.
Figure 7:
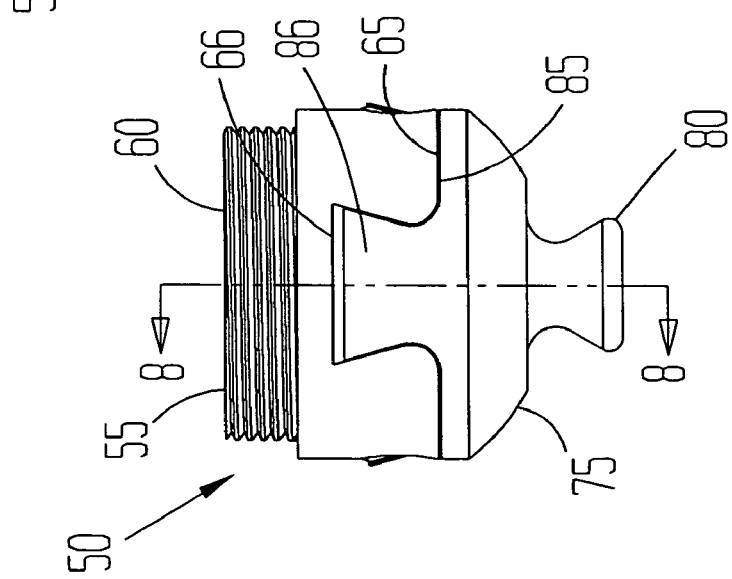
FIG. 7 is an end view of the present invention shown in FIG. 3.

Turning now to the present invention, an offset alignment device 50 is provided. As shown in FIGS. 3 and 4, the offset alignment device 50 generally has a first member 55 and a second member 75. The offset alignment device 50 further has a longitudinal axis 51 and an offsetting axis 52 that lies in a plane 53. Plane 53 is preferably generally perpendicular to longitudinal axis 51. The offset alignment device 50 is preferably made of steel or titanium alloy. However, it can be made of other materials without departing from the broad aspects of the present invention. Further, the offset alignment device 50 is preferably made in a computer numeric controlled, or CNC, process. However, the offset alignment device 50 can be made by different processes without departing from the broad aspects of the present invention.

Looking now at the offset alignment device 50 of the present invention in more detail, a first member 55 is provided. As best shown in FIGS. 5–11, 15 and 16, the first member 55 has a first end 60. The first end 60 of the first member 55 has a connector 61. In a preferred embodiment, the connector 61 has an exterior surface 62 that is threaded with threads 63. The first member 55 also has a second end 65. The second end 65 of the first member 55 has a channel 66 therethrough. The channel 66 has a channel longitudinal axis 67 that is preferably generally parallel to the offset alignment device 50 offsetting axis 52, and preferably generally perpendicular to the offset alignment device 50 longitudinal axis 51. The channel 66 has a first side 68, a second side 69 and a base 70. The first side 68 and second side 69 preferably extend from the base 70 at inwardly converging angles. However, the first side 68 and second side 69 could alternatively be generally perpendicular to the base 70. One or more screw holes 71 can be through the second end 65 from the exterior of the second end and into the channel 66. In a preferred embodiment, there is one screw hole 71 into the first side 68 of the channel 66 and one screw hole 71 into the second side 69 of the channel. The screw holes 71 are preferably oriented generally perpendicular to the channel longitudinal axis 67. Screws 72 are provided for being inserted into each screw hole 71.

A second member 75 is also provided as is best shown in FIGS. 5–13. The second member 75 has a first end 80. The first end 80 of the second member 75 has a connector 81. In a preferred embodiment, the connector 81 comprises a pyramid 82. The second member 75 also has a second end 85. The second end 85 of the second member 55 comprises a bar 86. The bar 86 defines a bar longitudinal axis 87. The bar longitudinal axis 87 is preferably generally parallel to the offset alignment device 50 offsetting axis 52, and preferably generally perpendicular to the offset alignment device 50 longitudinal axis 51. The bar 86 has a first side 88, a second side 89 and a top 90. The bar 86 is preferably shaped complementary to the channel 66 of the first member 55 of the offset alignment device 50. In this regard, the first side 88 and the second side 89 of the bar 86 preferably diverge from one another as they extend towards the top 90 of the bar. Alternatively, the first side 88 and second side 89 of the bar 86 could be generally perpendicular to the top 90 of the bar 86.

The first member 55 is designed to adjustably connect to the second member 75. In a preferred embodiment, this is accomplished by sliding the bar 86 of the second member 75 into the channel 66 of the first member 55. When connected in this manner, the bar longitudinal axis 87 is generally parallel to the channel longitudinal axis 67. As shown in FIGS. 10 and 1, the first member 55 can be adjusted either right to a first offset alignment or left to a second offset alignment with respect to the second member 75 to a longitudinal offset distance delta. Screws 72 can be inserted through screw holes 71 on the second end 65 of the first member 55. The screws 72 contact sides 88 and 89 of the bar 86 to frictionally hold the first member 55 stationary with respect to the second member 75.

The first member 55 is connectable to first prosthetic component. In a preferred embodiment, where the first member has a connector 61 comprising a threaded exterior surface 62, the first prosthetic component preferably has a complementary internally threaded end. One example is a conventional three prong adapter 30 with internally threaded end 32. However, other prosthetic components with internally threaded ends could be used instead of the three prong adapter 30 without departing from the broad aspects of the present invention. In this regard, the first end 60 is threadably and rotatably connected to the first prosthetic component. Hence, the channel longitudinal axis 67 is adjustable to any selected orientation with respect to the first prosthetic component. The channel longitudinal axis 67 will return to the same selected orientation with respect to the first prosthetic component after each successive ½ revolution of the first member 55 with respect to the first prosthetic component. However, the channel will move closer to or away from the first prosthetic component depending on whether the first member 55 is threaded further onto the threaded end of the first prosthetic component.

The second member 75 is connectable to a second prosthetic component. In a preferred embodiment, where the second member 75 has a connector 81 comprising a pyramid 82, the second prosthetic component preferably has a pyramidal receiver. One suitable example is a conventional pylon with fixed receiver 40 with a pyramidal receiver 41. However, other prosthetic components with pyramidal receivers can be used without departing from the broad aspects of the present invention. The pyramid 82 of the second member 75 is angularly adjustable relative to the pyramidal receiver in the conventional manner.

According to an alternative preferred embodiment of the present invention shown in FIG. 14, the second member 75 can comprise an alternative first end 100. The first end 100 has a connector 101 that comprises a receiver 102. The receiver 102 is a pyramidal receiver having screw holes 103 for receiving screws 104. In this regard, alternative first end 100 is intended for use with a prosthetic component comprising a pyramid (not shown).

According to a further alternative preferred embodiment of the present invention shown in FIG. 17, the first member 55 can comprise an alternative first end 110. The alternative first member first end 110 has a connector 11 that comprises an internally threaded clamp 112. The clamp 112 has threads 113 and a screw 114. The alternative first member first end 10 is intended for use with a prosthetic component having an externally threaded end. In this regard, the first member 55 is still adjustably and rotatably connected to the prosthetic component.

It is contemplated that both of the first member 55 and the second member 75 can be rotatably connected to the first and second prosthetic components.

The offset alignment device 50 of the present invention can replace existing components, or can be used in addition to existing prosthetic components, as space warrants. Nevertheless, no non-conventional components are necessary to use the offset alignment device 50 of the present invention with existing prosthetic components.

Figure 18:
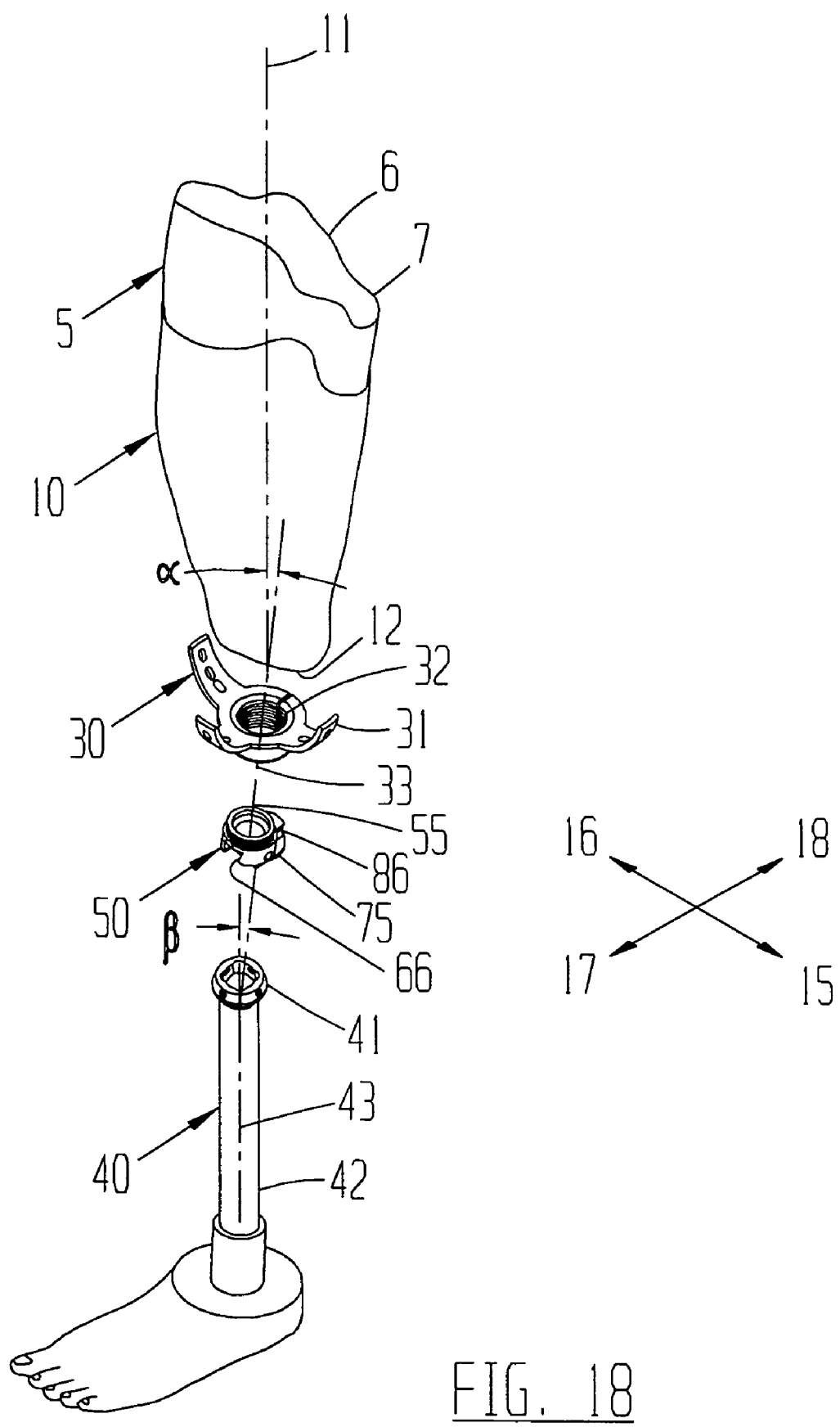
FIG. 18 is an exploded perspective view of the present invention shown in relation to existing prosthetic components.
Figure 19:
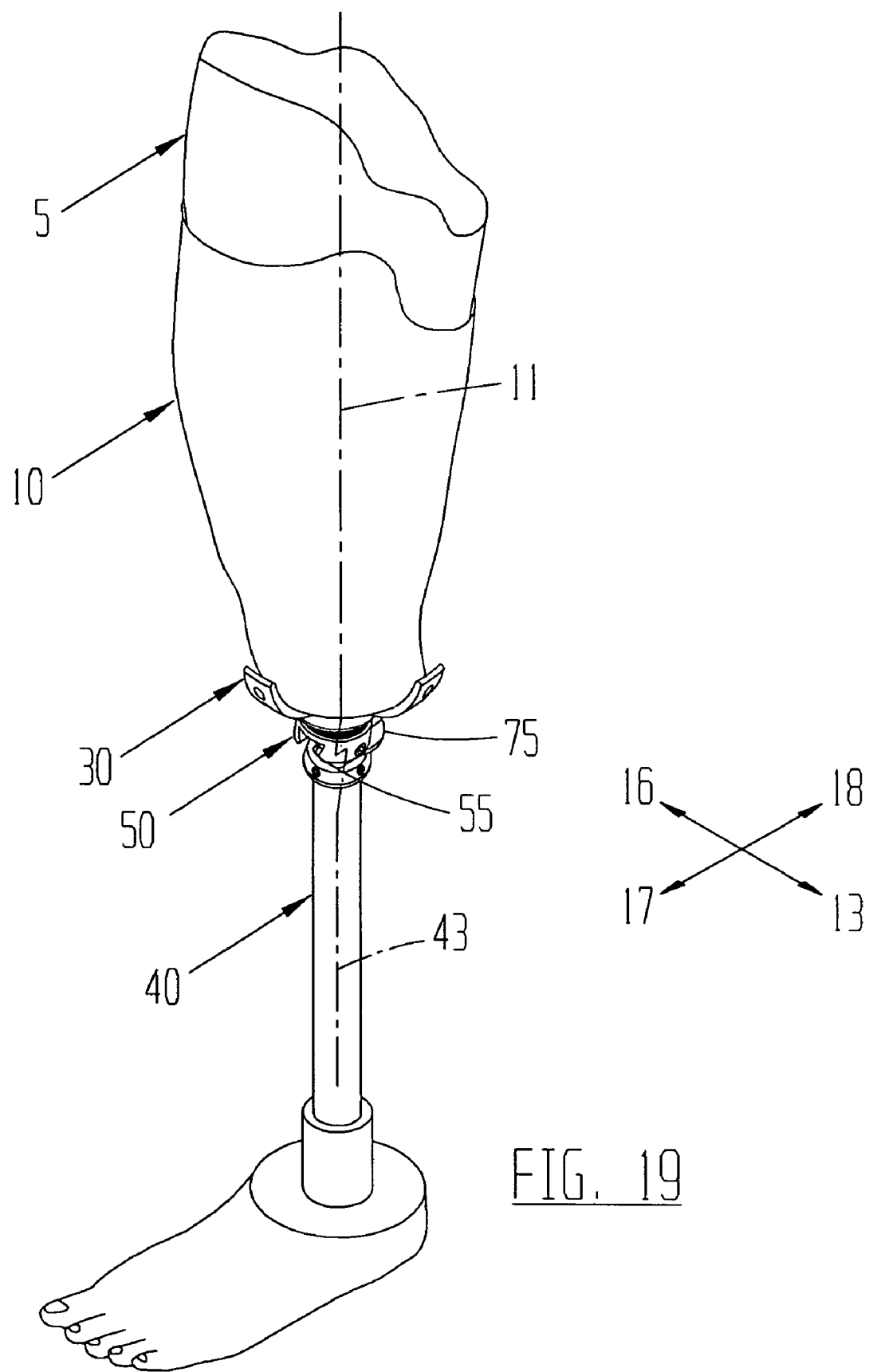
FIG. 19 is a perspective view of the present invention connected to prosthetic components and used to adjustably eliminate the offset between two prosthetic components.
Figure 20:
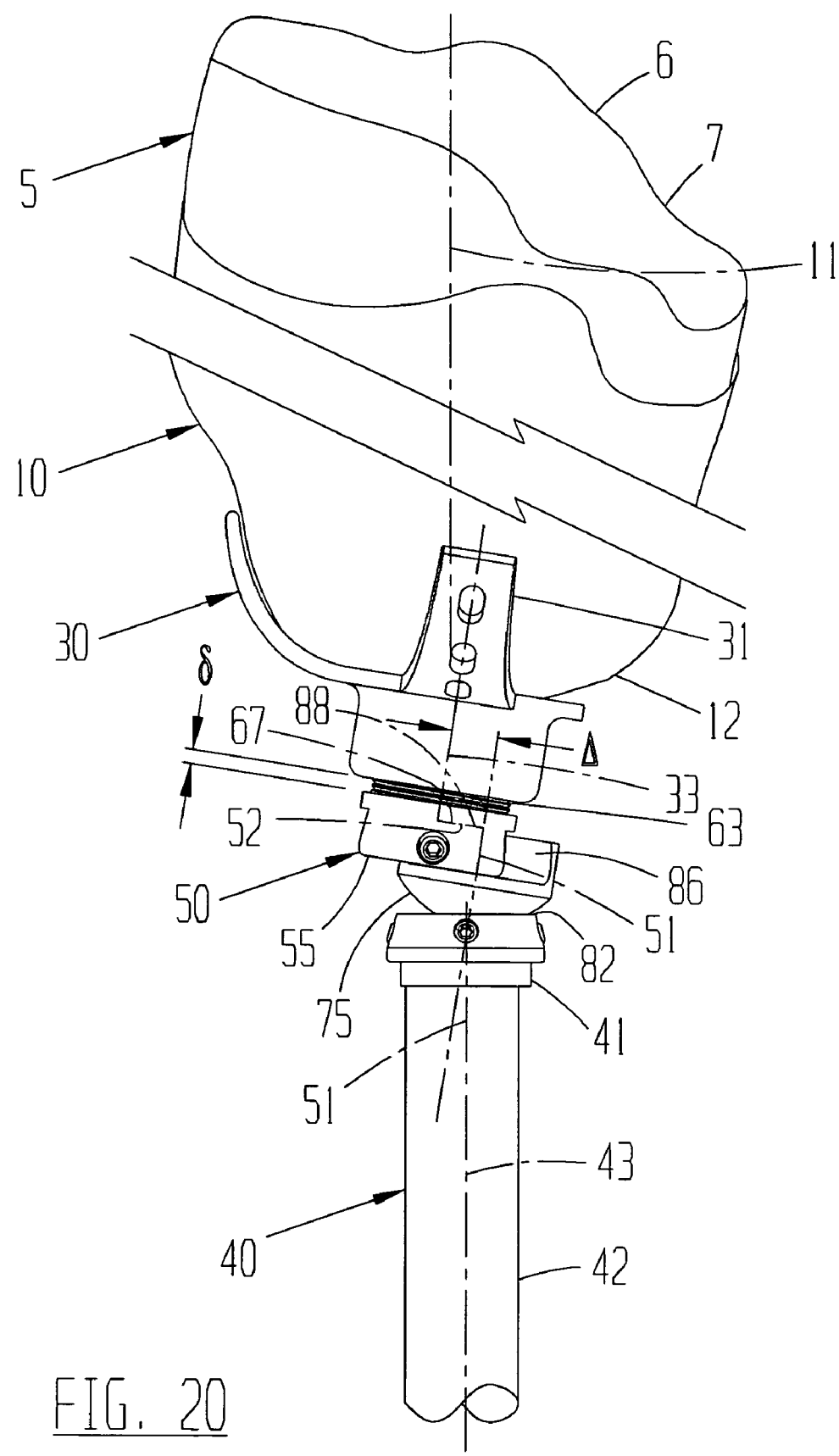
FIG. 20 is a close up side view of the present invention as shown in FIG. 19.

Turning now to use of the offset alignment device 50 of the present invention, best shown in FIGS. 18–20, the alignment device 50 aligns two prosthetic components that are connected to it. In this regard, the offset alignment device 50 is capable of adjusting a distance delta to overcome any offsetting distance between two prosthetic components. This is accomplished by making an adjustment along a single offsetting axis 52. A person must first determine the required or desired amount of adjustment to be made between the prosthetic components. This is done by considering the distance that the components are offset in the lateral or medial directions 15 or 16, and the anterior or posterior directions 17 or 18 and also the offset angle about a longitudinal axis. Then, the first member first end 60 is rotated with respect to the prosthetic component so that the channel longitudinal axis 67, and hence the offsetting axis 52, is properly aligned to the offset angle, which is within plane 53. It is appreciated that the offsetting axis 52 is selectably adjustable to all angles lying within the plane 53 that are generally perpendicular to the offset alignment device longitudinal axis 51. Next, the second member 75 is adjusted with respect to the first member 55 a selected distance delta along the offsetting axis 52. The last step is to lock the first member 55 into the selected position with respect to the second member 75. This locking step is accomplished by inserting screws 72 through screw holes 71 and contacting the end of the screws 72 against the sides 88 and 89 of the bar 86.

As an additional feature of the offset alignment device 50 of the present invention, once the proper orientation of the offsetting axis 52 is determined, the first member 55 can be further rotated in ½ revolutions with respect to the prosthetic component. After each successive ½ revolution, the offsetting axis 52 is again in the proper orientation. However, each successive ½ revolution does have an effect on the longitudinal offset distance gamma, shown in FIG. 20. Changing the longitudinal offset distance gamma changes the effective length or distance between two prosthetic components that are connected to the offset alignment device 50 of the present invention. Hence, according to this feature of the present invention, the overall length of a prosthetic component containing the present invention is longitudinally adjustable.

Thus it is apparent that there has been provided, in accordance with the invention, a device for offsetting prosthetic components that fully satisfies the objects, aims and advantages as set forth above. While the invention has been described in conjunction with specific embodiments thereof, it is evident that many alternatives, modification, and variations will be apparent to those skilled in the art in light of the foregoing description. Accordingly, it is intended to embrace all such alternatives, modifications, and variations as fall within the spirit and broad scope of the appended claims.

I claim:

1. An alignment device for being used with prosthetic components, said alignment device having an alignment device longitudinal axis and consisting of:
   A. a first monolithic member comprising:
      i. a first member first end connectable to a first prosthetic component; and
      ii. a first member second end having a channel therethrough with a channel first end and a channel second end, and a channel longitudinal axis; and
   B. a second monolithic member comprising:
      i. a second member first end connectable to a second prosthetic component; and
      ii. a second member second end comprising a bar with a bar first end and a bar second end, and having a longitudinal axis between said bar first end and said bar second end, said bar being received within and secured to said channel of said first member, said second member being selectably offset from said first member in one of a first direction generally parallel to said channel longitudinal axis and a second direction generally opposite of said first direction,
   wherein said bar first end is outside of said channel when said bar second end is between said channel first end and said channel second end when said first member is offset in said first direction from said second member,
   wherein said bar second end is outside of said channel when said bar first end is between said channel first end and said channel second end when said first member is offset in said second direction from said second member, and
   wherein one of said first member first end and said second member first end is threadably connectable to one of the first prosthetic component and the second prosthetic component, respectively, to allow said alignment device to be rotatably connected to said one of the first prosthetic component and the second prosthetic component such that the orientation of said channel longitudinal axis is selectably adjustable to any orientation lying in a plane that is generally perpendicular to said alignment device longitudinal axis.

2. The alignment device of claim 1 wherein said first member first end comprises a threaded external surface.

3. The alignment device of claim 1 wherein said first member first end comprises an internally threaded clamp.

4. The alignment device of claim 1 wherein said second member first end comprises a pyramid.

5. The alignment device of claim 1 wherein said second member first end comprises a pyramidal receiver.

6. The alignment device of claim 1 wherein said one of said first member first end and said second member first end that is threadably connectable to said one of the first prosthetic component and the second prosthetic component, respectively, can be further rotated a selected number of one half revolutions with respect to said one of the first prosthetic component and the second prosthetic component to maintain said selected orientation of said channel longitudinal axis and to selectably adjust the distance between the first prosthetic component connectable to said first member first end and the second prosthetic component connectable to said second member first end.

7. The alignment device of claim 1 wherein:
   said first member second end has a hole therethrough into said channel and that is perpendicular to said channel longitudinal axis, said hole capable of receiving a screw for contacting said bar for securing said bar in place within said channel.

* * * * *